United States Patent [19]

Albertins et al.

[11] Patent Number: 4,933,491

[45] Date of Patent: Jun. 12, 1990

[54] METHOD FOR PURIFYING A CRUDE NAPHTHALENE DICARBOXYLIC ACID

[75] Inventors: Rusins Albertins, Naperville; Stephen J. Pietsch, Oak Park; Juergen K. Holzhauer, Naperville; Hobe Schroeder, Warrenville, all of Ill.

[73] Assignee: Amoco Corporation, Chicago, Ill.

[21] Appl. No.: 415,634

[22] Filed: Oct. 2, 1989

[51] Int. Cl.$^5$ .................. C07C 51/265; C07C 51/487
[52] U.S. Cl. ..................................... 562/416; 562/417; 562/487; 562/488
[58] Field of Search ................ 562/416, 417, 487, 488

[56] References Cited

U.S. PATENT DOCUMENTS 3,592,847  7/1971  Gallivan et al. ............... 562/487 X
4,794,195 12/1988  Hayashi et al. ..................... 562/414

Primary Examiner—Werren B. Lone
Assistant Examiner—Vera C. Clarke
Attorney, Agent, or Firm—James R. Henes; William H. Magidson; Ralph C. Medhurst

[57] ABSTRACT

A method for purifying a naphthalene dicarboxylic acid produced by the liquid phase oxidation of a kialkylnaphthalene or partially oxidized derivative thereof in the presence of a catalyst comprising a bromine-containing component and at least one of a cobalt- or manganese-containing component.

32 Claims, No Drawings

METHOD FOR PURIFYING A CRUDE NAPHTHALENE DICARBOXYLIC ACID

BACKGROUND OF THE INVENTION

1. Field of the Invention

This invention relates generally to a method for purifying a crude naphthalene dicarboxylic acid and more particularly concerns a method for purifying a crude naphthalene dicarboxylic acid produced by the liquid-phase oxidation of a dialkylnaphthalene or partially oxidized derivative thereof in a solvent.

2. Discussion of the Prior Art

Fibers and films produced from polyethylenenaphthalate have improved strength and thermal properties relative to fibers and films produced from polyethyleneterephthalate and are especially useful in applications such as tire cords, magnetic tape backings and hot-fill containers. Naphthalene dicarboxylic acid, especially 2,6-naphthalene dicarboxylic acid, is employed as a monomer in the production of polyethylene naphthalate and is typically prepared by the catalyzed, liquid-phase oxidation of a dialkylnaphthalene, especially 2,6-dialkylnaphthalene.

The presence of impurities in the naphthalene dicarboxylic acid can obviously have a serious adverse effect on the physical or chemical properties or performance characteristics of any formulation containing the naphthalene dicarboxylic acid itself or any polymer formed from the naphthalene dicarboxylic acid. In addition, impurities in the naphthalene dicarboxylic acid can adversely affect polymerization processes to which the naphthalene dicarboxylic acid is subjected. Such impurities in the naphthalene dicarboxylic acid formed by the catalyzed, liquid-phase oxidation of a dialkylnaphthalene or partially oxidized derivative thereof are often organic impurities or by-products formed during the oxidation and inorganic impurities corresponding to metal components of the catalysts employed in the oxidation or formed therefrom.

Thus, removal of such impurities from the naphthalene dicarboxylic acid is highly desirable. However, the removal of organic and inorganic impurities from aromatic polycarboxylic acids formed by the catalyzed, liquid-phase oxidation of polyalkyl aromatics is typically very difficult, and the removal technique employed depends on the specific aromatic polycarboxylic acid from which the impurities are to be removed and the specific oxidation conditions and catalyst employed to make it.

For example, Gallivan et al., U.S. Pat. No. 3,592,847 disclose a process for the purification of terephthalic acid by dissolving the crude terephthalic acid in a solvent comprising at least 4.4 molar proportions of an anhydride of a lower alkanoic acid and by adding more than two molar proportions of a lower alkanoic acid per molar proportion of crude terephthalic acid. The lower alkanoic acid can be present in the solvent during dissolution of the terephthalic acid. Alternatively, sufficient water can be added to an anhydride solution containing excess anhydride to form the required amount of the alkanoic acid by reaction with the excess anhydride. Advantageously, the lower alkanoic acid produced as the terephthalic acid dissolves in the anhydride is removed during the dissolution, for example, by treating the mixture with a ketene to convert the acid formed back to the anhydride or by distillation of acid formed, in order to increase the amount of terephthalic acid dissolved. If desired, the terephthalic acid solution can be treated with a decolorizing agent such as adsorbent carbon prior to precipitating the purified product. However, a similar technique has not been disclosed or suggested for the purification of naphthalene dicarboxylic acids, which are much more difficult to purify.

Formation of the methyl ester is the best method known for purifying a naphthalene dicarboxylic acid. However, formation of the methyl ester alone does not afford a sufficiently pure monomer, and the methyl ester itself must be further purified, which purification can be time-consuming and involve relatively complex reaction schemes. Therefore, alternative methods of purification are highly desirable. In particular, removal of the impurities directly from the naphthalene dicarboxylic acids themselves offers the potential advantages of efficiency and economy. However, naphthalene dicarboxylic acids are especially difficult to purify because of their low solubility in most solvents.

OBJECTS OF THE INVENTION

It is therefore a general object of the present invention to provide an improved method which overcomes the aforesaid problems of prior art methods for purifying crude naphthalene dicarboxylic acid produced by the liquid-phase oxidation of a dialkylnaphthalene or partially oxidized derivative thereof with an oxygen-containing gas in a solvent and in the presence of an oxidation catalyst comprising a bromine-containing component and at least one cobalt- or manganese-containing component.

More particularly, it is an object of the present invention to provide a fast and simple method for purifying crude naphthalene dicarboxylic acid produced by the aforesaid liquid-phase oxidation of a dialkylnaphthalene or partially oxidized derivative thereof which affords a purified naphthalene dicarboxylic acid product having reduced contents of organic and inorganic impurities.

Other objects and advantages of the invention will become apparent upon reading the following detailed description and appended claims.

SUMMARY OF THE INVENTION

These objects are achieved by the present invention which is an improvement in a method for producing a naphthalene dicarboxylic acid comprising oxidizing a dialkylnaphthalene wherein each alkyl group may be the same or different and is methyl, ethyl or propyl, or a partially oxidized derivative thereof, with an oxygen-containing gas in a solvent in the liquid phase at an elevated temperature and pressure and in the presence of an oxidation catalyst comprising a bromine component and at least one of a cobalt- or manganese-containing component to form a crude naphthalene dicarboxylic acid. The improvement comprises purifying the resulting solid crude naphthalene dicarboxylic acid by: (a) reacting the crude naphthalene dicarboxylic acid with a first lower alkanoic anhydride at a mole ratio in the range of from about 1 to about 2 moles of the first lower alkanoic anhydride per mole of crude naphthalene dicarboxylic acid, and at a temperature in the range of from about 100° C. to about 200° C., to thereby form (1) a reaction product of the crude naphthalene dicarboxylic acid and first lower alkanoic anhydride which is soluble in the excess unreacted first lower alkanoic anhydride and (2) an alkanoic acid formed from the first lower alkanoic anhydride; (b) reacting the aforesaid dissolved reaction product with from about 1 to about 2 moles of water or an alkanoic acid containing from 2 to 5 carbon atoms, per mole of crude naphthalene dicarboxylic acid employed in step (a), and at a temperature in the range of from about 20° C. to about 200° C., to thereby form the purified form of the naphthalene dicarboxylic acid, which was employed in step (a) which crystallizes to produce a solid-liquid mixture; and (c) removing solid purified naphthalene dicarboxylic acid from the resulting solid-liquid mixture at a temperature in the range of from about 20° C. to about 200° C.

DETAILED DESCRIPTION OF THE PREFERRED EMBODIMENTS

Any dialkylnaphthalene wherein the alkyl substituent contains from 1 to 3 carbon atoms or the partially oxidized derivative thereof, is suitable for use as the feedstock in the oxidation step or the method of this invention. Suitable partially oxidized derivatives include formylmethylnaphthalene, acetylmethylnaphthalene, carboxymethylnaphthalene, diformylnaphthalene, diacetylnaphthalene, and dicarboxynaphthalene. Preferably, the oxidizable substituents are in the 2,6-position on the naphthalene ring. Preferably, the alkyl group is a methyl or ethyl group, and, more preferably, the feedstock is a dimethylnaphthalene. Most preferably, the feedstock is 2,6-dimethylnaphthalene and 2,6-naphthalene dicarboxylic acid is produced.

Suitable solvents for use in the oxidation step of the method of this invention include benzoic, any aliphatic $C_2$-$C_6$ monocarboxylic acid such as acetic acid, propionic acid, n-butyric acid, isobutyric acid, n-valeric acid, trimethylacetic acid, and caproic acid, and water, and mixtures thereof. Preferably, the solvent is a mixture of acetic acid and water, which more preferably contains from 1 to 20 weight percent of water, as introduced into the oxidation reactor. Since heat generated in the highly exothermic liquid-phase oxidation is dissipated at least partially by vaporization of solvent in the oxidation reactor, some of the solvent is withdrawn from the oxidation reactor as a vapor, which is then condensed and recycled to the reactor.

In addition, some solvent is withdrawn from the oxidation reactor as a liquid in the product stream. After separation of the crude naphthalene dicarboxylic acid product from the product stream, at least a portion of the mother liquor (solvent) in the resulting product stream is generally recycled to the oxidation reactor.

The source of molecular oxygen employed in the oxidation step of the method of this invention can vary in molecular oxygen content from that of air to oxygen gas. Air is the preferred source of molecular oxygen. In order to avoid the formation of explosive mixtures, the oxygen-containing gas fed to the reactor should provide an exhaust gas-vapor mixture containing from 0.5 to 8 volume percent oxygen (measured on a solvent-free basis). For example, a feed rate of the oxygen-containing gas sufficient to provide oxygen in the amount of from 1.5 to 2.8 moles per methyl group will provide such 0.5 to 8 volume percent of oxygen (measured on a solvent-free basis) in the gas-vapor mixture in the condenser.

The catalyst employed in the oxidation step of the method of this invention comprises a bromine-containing component and at least one of a cobalt- and manganese-containing component, and can additionally comprise accelerators known in the art. Preferably, the catalyst comprises cobalt-, manganese-, and bromine-containing components. The ratio of cobalt (calculated as elemental cobalt) in the cobalt component of the catalyst-to-the dialkylnaphthalene or partially oxidized derivative thereof in the liquid-phase oxidation is in the range of from about 0.1 to about 100 milligram atoms (mga) per gram mole of dialkylnaphthalene or partially oxidized derivative thereof. The ratio of manganese (calculated as elemental manganese) in the manganese component of the catalyst-to-cobalt (calculated as elemental cobalt) in the cobalt component of the catalyst in the liquid-phase oxidation is in the range of from about 0.1 to about 10 mga per mga of cobalt. The ratio of bromine (calculated as elemental bromine) in the bromine component of the catalyst-to-total cobalt and manganese (calculated as elemental cobalt and elemental manganese) in the cobalt and manganese components of the catalyst in the liquid-phase oxidation is in the range of from about 0.1 to about 1.5 mga per mga of total cobalt and manganese.

Each of the cobalt and manganese components can be provided in any of its known ionic or combined forms that provide soluble forms of cobalt, manganese, and bromine in the solvent in the reactor. For example, when the solvent is an acetic acid medium, cobalt and/or manganese carbonate, acetate tetrahydrate, and/or bromide can be employed. The 0.1:1.0 to 1.5:1.0 bromine-to-total cobalt and manganese milligram atom ratio is provided by a suitable bromine sources include elemental bromine ($Br_2$), or ionic bromide (e.g., HBr, NaBr, KBr, $NH_4Br$, etc.), or organic bromides which are known to provide bromide ions at the operating temperature of the oxidation (e.g., bromobenzenes, benzyl-bromide, mono- and di-bromoacetic acid, bromoacetyl bromide, tetrabromoethane, ethylene-di-bromide, etc.). The total bromine in molecular bromine and ionic bromide is used to determine satisfaction of the elemental bromine-to-total cobalt and manganese milligram atom ratio of 0.1:1.0 to 1.5:1.0. The bromine ion released from the organic bromides at the oxidation operating conditions can be readily determined by known analytical means. Tetrabromoethane, for example, at operating temperatures of 170° C. to 225° C. has been found to yield about 3 effective gram atoms of bromine per gram mole.

In operation, the minimum pressure at which the oxidation reactor is maintained is that pressure which will maintain a substantial liquid phase of the dialkylnaphthalene or partially oxidized derivative thereof and at least 70 percent of the solvent. The dialkylnaphthalene or partially oxidized derivative thereof and solvent not in the liquid phase because of vaporization is removed from the oxidation reactor as a vapor-gas mixture, condensed, and then returned to the oxidation reactor. When the solvent is an acetic acid-water mixture, suitable reaction gauge pressures in the oxidation reactor are in the range of from about 0 kg/cm² to about 35 kg/cm², and typically are in the range of from about 10 kg/cm² to about 30 kg/cm². The temperature range within the oxidation reactor is generally from about 120° C., preferably from about 150° C., to about 240° C., preferably to about 230° C. The solvent residence time in the oxidation reactor is generally from about 20 to about 150 minutes and preferably from about 30 to about 120 minutes.

The oxidation of the method of this invention can be performed either on a batch, continuous, or semicontinuous mode. In the batch mode, the dialkylnaphthalene or its partially oxidized derivatives, solvent and the catalyst components are initially introduced batchwise into the reactor, and the temperature and pressure of the reactor contents are then raised to the desired levels therefor for the commencement of the oxidation reaction. Air is introduced continuously into the reactor. After commencement of the oxidation reaction—for example, after all of the dialkylnaphthalene or its partially oxidized derivative has been completely introduced into the reactor, the temperature of the reactor contents is raised.

In the continuous mode, each of the dialkylnaphthalene or partially oxidized derivative thereof, air, solvent, and catalyst are continuously introduced into the reactor, and a product stream comprising naphthalene dicarboxylic acid and catalyst components dissolved in the solvent is withdrawn from the reactor. In the semicontinuous mode, the solvent and catalyst are initially introduced into the reactor and then the dialkyl naphthalene or its partially oxidized derivative and air are continuously introduced into the reactor.

Thereafter, the product stream in the continuous mode or the reactor contents in the batch or semicontinuous mode are cooled to a temperature in the range of from about 80° C. to about 105° C. in at least one step and in at least one crystallizer such that essentially all of the naphthalene dicarboxylic acid crystallizes in the solvent. Following crystallization, the resulting slurry of naphthalene dicarboxylic acid in the mother liquor is separated, typically by centrifugation, at a temperature in the range of from about 80° C. to about 105° C. Generally, the separation is performed at essentially the same temperatures as the final crystallization temperature.

The resulting separated crude naphthalene dicarboxylic acid is first dissolved in a first lower alkanoic anhydride of an alkanoic acid having from two to five carbon atoms. Suitable anhydrides include acetic anhydride, propionic anhydride, n-butyric anhydride, isobutyric anhydride, n-valeric anhydride, and mixtures of two or more thereof. Preferably, the first lower alkanoic anhydride is acetic anhydride. The crude naphthalene dicarboxylic acid and first lower alkanoic anhydride are employed at a mole ratio in the range of from about 0.01, preferably from about 0.02, to about 0.20, preferably to about 0.1 moles of crude naphthalene dicarboxylic acid per mole of the first lower alkanoic anhydride.

Although the exact mechanism of the dissolution is unknown, it is believed that at least some of the crude naphthalene dicarboxylic acid reacts with the first lower alkanoic anhydride solvent to form a reaction product, in particular, a mixed anhydride, of the crude naphthalene dicarboxylic acid and the alkanoic acid corresponding to the first lower alkanoic anhydride. For the purposes of the present application, the soluble material resulting from this treatment of the crude acid with the first lower alkanoic anhydride solvent is referred to as the reaction product of the crude naphthalene dicarboxylic acid with the first lower alkanoic anhydride solvent.

The temperature employed to react or dissolve the crude naphthalene dicarboxylic acid depends upon the specific naphthalene dicarboxylic acid and first lower alkanoic anhydride and the relative amounts of each thereof employed. When 2,6-naphthalene dicarboxylic acid is being purified and acetic anhydride is the first lower alkanoic anhydride employed, the temperature of this step is in the range of from about 80° C., preferably from about 100° C., to about 200° C., preferably to about 180° C.

An alkanoic acid corresponding to the first lower alkanoic anhydride is also produced in this dissolution or reaction step. Preferably, the alkanoic acid produced during the dissolution or reaction of the crude naphthalene dicarboxylic acid in the first lower alkanoic anhydride is removed during the dissolution or reaction process. Because the dissolution of the crude naphthalene dicarboxylic acid in the lower alkanoic anhydride (and the reaction of the crude naphthalene dicarboxylic acid with the first lower alkanoic anhydride) is an equilibrium process, removal of the alkanoic acid produced during this step permits the dissolution (and/or reaction) of substantially higher concentrations of the crude naphthalene dicarboxylic acid with the first lower alkanoic anhydride. It is highly preferable in the method of the present invention to remove the alkanoic acid produced during the dissolution or reaction as it is being produced.

The alkanoic acid produced during this step can be removed as it is being produced by any suitable means such as by treating the mixture with a ketene at an elevated temperature—for example, above about 110° C., preferably above about 130° C.—to covert the alkanoic acid formed back to an anhydride. Suitable ketenes for use for this purpose are those having from two to five carbon atoms, including ketene, methyl ketene, ethyl ketene, and dimethyl ketene. In the alternative, this dissolution or reaction step can be performed at a temperature at or above the boiling point of the alkanoic acid being produced, and therefore the alkanoic acid is distilled off as it is being produced. When the alkanoic acid is removed by distillation, it is desirable to charge additional first lower alkanoic anhydride in order to compensate for anhydride values that are lost in the form of the distilled alkanoic acid. Such additional first lower alkanoic anhydride can be added either during the distillation or prior to the distillation.

When the aforesaid reaction product is completely solubilized, it is substantially completely converted back to the naphthalene dicarboxylic acid from which it was formed and which is being purified by the method of this invention, by the addition of at least a sufficient amount of either water or of a lower alkanoic acid to effect this conversion, at a temperature in the range of from about 20° C., preferably from about 120° C., to about 200° C., preferably to about 180° C. Such sufficient amount is in the range of from about 1 to about 2 moles of water or of the lower alkanoic acid per mole of the crude naphthalene dicarboxylic acid originally employed in the purification method of this invention. The lower alkanoic acids that are useful for this conversion are those having from 2 to 5 carbon atoms. Suitable such acids include acetic acid, propionic acid, n-butyric acid, isobutyric acid, n-valeric acid, and cyclopropylcarboxylic acid. Preferably, the lower alkanoic acid employed is the acid corresponding to the aforesaid first lower alkanoic anhydride used as described hereinabove, for example, acetic acid with acetic anhydride or n-butyric acid with n-butyric anhydride.

The resulting purified naphthalene dicarboxylic acid is insoluble in the resulting liquid mixture and crystallizes and then is separated and recovered, for example, by filtration or centrifugation at a temperature in the range of from about 20° C., preferably from about 80° C., to about 200° C., preferably to about 180° C.

Although water is suitable to convert the aforesaid purified reaction product back to the naphthalene dicarboxylic acid from which it was formed, water would also react with the aforesaid first lower alkanoic anhydride and hence would result in a greater consumption of solvent than if an aforesaid lower alkanoic acid were used to convert the aforesaid purified reaction product. Therefore, it is preferred to use an aforesaid lower alkanoic acid to convert the aforesaid purified reaction product back to the naphthalene dicarboxylic acid from which it was formed.

In a preferred embodiment of the method of this invention, after the crude naphthalene dicarboxylic acid is substantially completely dissolved or reacted in the aforesaid first lower alkanoic anhydride, the resulting solution is cooled to a temperature in the range of from about 60° C., preferably from about 40° C., to about −30° C., preferably to about −15° C., in order to crystallize the resulting purified reaction product of the crude naphthalene dicarboxylic acid and the first lower alkanoic anhydride, which is then separated and recovered, for example, by filtration or centrifugation at a temperature in the range of from about 60° C., preferably from about 40° C., to about −30° C., preferably to about −15° C.

The separated solid aforesaid reaction product is then dissolved in a second lower alkanoic anhydride of an alkanoic acid having from two to five carbon atoms at a temperature in the range of from about 20° C., preferably from about 100° C., to about 200° C., preferably to about 180° C. Suitable anhydrides include acetic anhydride, propionic anhydride, n-butyric anhydride, isobutyric anhydride, n-valeric anhydride, and mixtures of two or more thereof. Preferably, the second lower alkanoic anhydride is the same as the first lower alkanoic anhydride. The amount of second lower alkanoic anhydride employed is in the range of from about 5, preferably from about 10, to about 50, preferably to about 20 moles, per mole of the crude naphthalene dicarboxylic acid originally employed in the method of this invention.

As described hereinabove for crystallization of the purified naphthalene dicarboxylic acid from the aforesaid first lower alkanoic anhydride, when the aforesaid reaction product is completely solubilized in the second lower alkanoic anhydride, it is substantially completely converted back to the naphthalene dicarboxylic acid from which it was formed and which is being purified by the method of this invention, by the addition of at least a sufficient amount of either water or a lower alkanoic acid to effect this conversion, at a temperature in the range of from about 20° C., preferably from about 120° C., to about 200° C., preferably to about 180° C. Such sufficient amount is in the range of from about 1 to about 2 moles of water or of the lower alkanoic acid per mole of the crude naphthalene dicarboxylic acid originally employed in the purification method of this invention. The lower alkanoic acids that are useful for this conversion are those having from 2 to 5 carbon atoms. Suitable such acids include acetic acid, propionic acid, n-butyric acid, isobutyric acid, n-valeric acid, and cyclopropylcarboxylic acid. Preferably, the lower alkanoic acid employed is the acid corresponding to the aforesaid second lower alkanoic anhydride used as described hereinabove, for example, acetic acid with acetic anhydride or n-butyric acid with n-butyric anhydride.

The resulting purified naphthalene dicarboxylic acid is insoluble in the resulting liquid mixture and precipitates and then is separated and recovered, for example, by filtration or centrifugation at a temperature in the range of from about 20° C., preferably from about 80° C., to about 200° C., preferably to about 180° C.

Although water is suitable to convert the aforesaid purified reaction product back to the naphthalene dicarboxylic acid from which it was formed, water would also react with the second lower alkanoic anhydride and hence would result in a greater consumption of solvent than if an aforesaid lower alkanoic acid were used to convert the aforesaid purified reaction product. Therefore, it is preferred to use an aforesaid lower alkanoic acid to convert the aforesaid purified reaction product back to the naphthalene dicarboxylic acid from which it was formed.

In a preferred embodiment of the method of this invention, after the crude naphthalene dicarboxylic acid is substantially completely dissolved or reacted in the first lower alkanoic anhydride and before either (a) adding water or a lower alkanoic anhydride to crystallize the purified naphthalene dicarboxylic acid in the general method of this invention or (b) cooling the solution of the reaction product of the naphthalene dicarboxylic acid in the first lower alkanoic anhydride to crystallize the aforesaid reaction product in the aforesaid preferred embodiment of the method of this invention, any undissolved solid impurities are removed while maintaining the temperature of the solid-liquid mixture in the range of from about 80° C., preferably from about 100° C., to about 200° C., preferably to about 180° C., by any suitable convenient means, for example, by filtration or centrifugation. More preferably, a filter aid such as Celite is employed in such filtration. For example, the filter could be precoated with a filter aid.

In a further preferred embodiment of the method of this invention, after the crude naphthalene dicarboxylic acid is substantially completely dissolved or reacted in the first lower alkanoic anhydride and before either (a) adding water or a lower alkanoic acid to the solution of the reaction product of the naphthalene dicarboxylic acid in the first lower alkanoic anhydride to precipitate purified naphthalene dicarboxylic acid in the general method of this invention, or (b) cooling the solution of the reaction product of the naphthalene dicarboxylic acid in the first lower alkanoic anhydride to crystallize the reaction product of the naphthalene dicarboxylic acid in the aforesaid preferred embodiment of the method of this invention, the solution is hydrogenated in the presence of a hydrogenation catalyst at an elevated temperature and pressure and typically in a fixed catalyst bed. The temperature employed in the hydrogenation step is in the range of from about 80° C., preferably from about 100° C., to about 200° C., preferably to about 180° C.

The pressure employed in the hydrogenation step depends primarily upon the temperature employed therein. Inasmuch as the temperatures at which practical amounts of the aforesaid reaction product are dissolved in the aforesaid first lower alkanoic anhydride solvent are substantially above the normal boiling point of the solvent, the process pressures are necessarily considerably above atmospheric pressure in order to maintain the solution in liquid phase. If the hydrogenation reactor is hydraulically full, the reactor pressure can be controlled by the feed pumping rate. If the reactor has a head space, the reactor pressure can be maintained by gaseous hydrogen alone or in admixture with an inert gas such as water vapor and/or nitrogen in the head space. The use of an inert gas in admixture with hydrogen also can provide an advantageous means for modulating the reactor hydrogen partial pressure, especially at relatively low hydrogen partial pressures. To this end, the inert gas preferably is admixed with hydrogen prior to introduction into the reactor. In general, the reactor pressure during hydrogenation can be in the range of about 10 to about 1,000 pounds per square inch gauge (psig), and usually is in the range of about 25 psig to about 500 psig.

The reactor employed in the hydrogenation step can be operated in several modes. For example, a predetermined liquid level can be maintained in the reactor, and hydrogen can be fed in, for any given reactor pressure, at a rate sufficient to maintain predetermined liquid level. The difference between the actual reactor pressure and the vapor pressure of the solution present is the hydrogen partial pressure in the reactor vapor space. Alternatively, if hydrogen is fed in admixture with an inert gas such as nitrogen, the difference between the actual reactor pressure and the vapor pressure of the solution present is the combined partial pressure of hydrogen and the inert gas admixed therewith. In this case the hydrogen partial pressure can be calculated from the known relative amounts of hydrogen and inert gas present in the admixture.

In yet another operating mode, the hydrogenation reactor can be filled with the solution so as to provide no reactor vapor space. That is, the reactor can be operated as a hydraulically full system with dissolved hydrogen being fed to the reactor by flow control. In such an instance, the solution hydrogen concentration can be modulated by adjusting the hydrogen flow rate to the reactor. If desired, a pseudo-hydrogen partial pressure value can be calculated from the solution hydrogen concentration which, in turn, can be correlated with the hydrogen flow rate to the reactor.

In the operating mode where process control is effected by adjusting the hydrogen partial pressure, the hydrogen partial pressure in the reactor preferably is in the range of about 10 psi to about 200 psi, or higher, depending upon the service pressure rating of the reactor, the degree of contamination of the impure naphthalene dicarboxylic acid initially employed, the activity and age of the particular catalyst employed, and like processing considerations.

In the operating mode where process control is effected by adjusting directly the hydrogen concentration in the feed solution, the latter usually is less than saturated with respect to hydrogen, and the reactor itself is hydraulically full. Thus, an adjustment of the hydrogen flow rate to the reactor will result in the desired control of hydrogen concentration in the solution.

In general, the amount of hydrogen supplied to the hydrogen reactor under reaction conditions is, of course, sufficient to effect the desired hydrogenation.

Catalysts that are suitable for use in the aforesaid purification step are insoluble under the conditions employed therein and comprise at least one supported or unsupported Group VIII noble metal, whose class includes palladium, rhodium, ruthenium, osmium, iridium, and platinum. Preferably, the noble metal is at least one of palladium and rhodium. Preferably, the catalyst comprises a solid support. Suitable support materials include active carbon, charcoal, alumina, silica, titania, magnesia, and mixtures thereof. Preferred support materials include active carbon and charcoal. Typically, the catalyst carrier is active carbon, usually that derived from coconut charcoal in the form of granules having a surface area of at least about 600 $m^2/g$ ($N_2$; BET Method), preferably about 800 $m^2/g$ to about 1,500 $m^2/g$. However, other porous carbonaceous supports or substrates can be used as long as the surface area requirements can be met. In addition to coconut charcoal, activated carbon derived from other plant or from animal sources can be utilized.

The noble metal component is present on the carrier at a concentration level in the range of about 0.01 weight percent to about 2 weight percent, based on the total weight of the catalyst, i.e., metal plus active carbon carrier, and calculated as the elemental noble metal. Preferably, the catalyst metal loading is about 0.5 weight percent. A typical catalyst of palladium on a support comprises from about 0.01 to about 2 weight percent of palladium, based on the total weight of the catalyst and calculated as elemental metal. The support or carrier for the palladium is porous and inert, and preferably is active carbon having a surface area of about 600 $m^2/g$ to about 1,500 $m^2/g$. Suitable supports for Pd/C hydrogenation catalysts are well-known.

A suitable palladium-on-carbon catalyst can be obtained, for example, from Engelhard Corporation, Newark, N.J., under the designation "Palladium on Activated Carbon Granules (Carbon Code CG-5)." Similarly, suitable rhodium-on-carbon catalysts can be obtained from Englehard Corporation, under the designations "Rhodium on Activated Carbon Granules (Carbon Code CG-5)" and "Rhodium on Activated Carbon Granules (Carbon Code CG-21)." Both of these catalysts have a BET; $N_2$ surface area of about 1,000 $m^2/g$ and have a particle size of $4 \times 8$ mesh, U.S. Sieve Series. Other suitable rhodium-on-carbon catalysts of similar size and surface area are available from Johnson Matthey Inc., Seabrook, N.H., under the designation "11766 Rhodium, 1% on Steam Activated Carbon Granules, Anhydrous."

The space velocity reported as weight of solution per weight of hydrogenation catalyst per hour in the purification step is from about 1 hour$^{-1}$ to about 50 hours$^{-1}$, preferably from about 5 hours$^{-1}$ to about 25 hours$^{-1}$. The residence time of the solution in the hydrogenation catalyst bed varies, depending upon the activity of the catalysts present.

In a further preferred embodiment of the method of this invention, after the crude naphthalene dicarboxylic acid is substantially completely dissolved or reacted in the first lower alkanoic anhydride and before either (a) adding water or a lower alkanoic acid to the solution or the reaction product of the naphthalene dicarboxylic acid in the first lower alkanoic anhydride to precipitate purified naphthalene dicarboxylic acid in the general method of this invention, or (b) cooling the solution of the reaction product of the naphthalene dicarboxylic acid in the first lower alkanoic anhydride to crystallize the reaction product of the naphthalene dicarboxylic acid in the aforesaid preferred embodiment of the method of this invention, activated carbon is admixed with the solution at a weight ratio in the range of from about 0.005, preferably from about 0.01, to about 0.05, preferably to about 0.04 of activated carbon per part by weight of the crude naphthalene dicarboxylic acid originally employed, and then the liquid is separated from the active carbon. For example, the activated carbon can be separated when solids are removed from the solution of the aforesaid reaction product in the first lower alkanoic anhydride.

In a further preferred embodiment of the aforesaid preferred embodiment of the method of this invention, after the aforesaid solid reaction product is separated from the first lower alkanoic anhydride, the solid reaction product is washed with a third lower alkanoic anhydride of an alkanoic acid having from 2 to 5 carbon atoms at a temperature in the range of from about 60° C. to about −30° C., preferably to about −15° C., before the solid reaction product is dissolved in the second lower alkanoic anhydride. Anhydrides that are suitable for use as the third lower alkanoic anhydride include acetic anhydride, propionic anhydride, n-butyric anhydride, isobutyric anhydride, n-valeric anhydride and mixtures of two or more thereof. Preferably, the third lower alkanoic anhydride is the same as the second lower alkanoic anhydride.

In yet another preferred embodiment of the method of this invention, after the solid purified naphthalene dicarboxylic acid is separated from the second lower alkanoic anhydride, the solid purified acid is dried at a temperature in the range of from about 70° C., preferably from about 100° C., to about 200° C., preferably to about 150° C.

The present invention will be more clearly understood from the following specific examples.

EXAMPLE 1

Example 1 involved the semicontinuous oxidation in three separate runs of 2,6-dimethylnaphthalene in a solvent in the liquid phase containing 95 weight percent of acetic acid and 5 weight percent of water in a 5 gallon autoclave. 2,6-dimethylnaphthalene was introduced into the reactor at a rate of 707, 680, and 702 grams per hour in each of the three runs. The weight ratio of total amount of solvent-to-total amount of 2,6-dimethylnaphthalene introduced during each run was 6.0:1.0, 6.2:1.0 and 5.7:1.0. In each case, the catalyst comprised cobalt, manganese and bromine components. The weight ratio of cobalt (calculated as elemental cobalt) in the cobalt component of the catalyst-to-2,6-dimethylnaphthalene was 0.009:1, 0.0093:1, and 0.0086:1. The weight ratio of manganese (calculated as elemental manganese) in the manganese components of the catalyst-to-cobalt (calculated as elemental cobalt) in the cobalt component was 2.8:1, 2.8:1, and 2.8:1 in the three runs. The weight ratio of bromine (calculated as elemental bromine) in the bromine component-to-total cobalt and manganese (calculated as the elemental metals) in the cobalt and manganese components were 0.71:1, 0.71:1, and 0.71:1 for the three runs. In each run, the residence time of the 2,6-dimethylnaphthalene in the reactor was 90 minutes. The reaction temperature was 385° F., 400° F., and 415° F. in the three runs. A stream containing dissolved catalyst components, 2,6-naphthalene dicarboxylic acid and any unreacted 2,6-dimethylnaphthalene was passed to a secondary oxidation reactor, where in each run the residence time of the 2,6-dimethylnaphthalene in the reactor was 30 minutes. The secondary oxidation was performed at a temperature of 370° F., 385° F., and 400° F. in the runs. The characteristics of the resulting crude 2,6-naphthalene dicarboxylic acid are shown in Table 1.

EXAMPLE 2

Example 2 involved the semicontinuous oxidation in three separate runs of 2,6-dimethylnaphthalene in a solvent in the liquid phase containing 89, 86.9 and 86.2 weight percent of acetic acid and 11.0, 13.1 and 13.8 weight percent of acetic acid and 11.0, 13.1 and 13.8 weight percent of water, respectively, in a 5 gallon autoclave. 2,6-dimethylnaphthalene was introduced into the reactor at a rate of 635, 1991, and 2068 grams per hour in each of the three runs. The weight ratio of total amount of solvent-to-total amount of 2,6-dimethylnaphthalene introduced during each run was 6.65 grams per gram, 4.0 grams per gram, and 4.0 grams per gram. In each case, the catalyst comprised cobalt, manganese and bromine components. The weight ratio of cobalt (calculated as elemental cobalt) in the cobalt component of the catalyst-to-2,6-dimethylnaphthalene was 0.0067 gram per gram, 0.0088 gram per gram, and 0.0076 gram per gram. The weight ratio of manganese (calculated as elemental manganese) in the manganese components of the catalyst-to-cobalt (calculated as elemental cobalt) in the cobalt component was 2.80 grams per gram, 2.80 grams per gram, and 2.80 grams per gram in the three runs. The weight ratio of bromine (calculated as elemental bromine) in the bromine component-to-total cobalt and manganese (calculated as the elemental metals) in the cobalt and manganese components were 0.71 gram per gram for each of the three runs. The residence times of the 2,6-dimethylnaphthalene in the reactor were 101, 42, and 42 minutes in the three runs. The reaction temperatures were 400° F., 400° F. and 408° F. in the runs. A stream containing dissolved catalyst components, 2,6-naphthalene dicarboxylic acid and any unreacted 2,6-dimethylnaphthalene was passed to a secondary oxidation reactor, where in each run the residence time of the 2,6-dimethylnaphthalene in the reactor was 50, 21 and 21 minutes. The secondary oxidation was performed at temperatures of 372° F., 371° F., and 373° F. in the runs. The characteristics of the resulting crude 2,6-naphthalene dicarboxylic acid are shown in Table 2.

EXAMPLE 3

50 grams of crude 2,6-naphthalene dicarboxylic acid prepared by the method of Example 1 were combined with 1000 grams of boiling acetic anhydride. The resulting solution was filtered at a temperature of 135° C. to remove any undissolved solids. Then, to the resulting filtrate at about its boiling point, 1216 grams of glacial acetic acid at 118° C. were added to precipitate 2,6-naphthalene dicarboxylic acid. This acid was recovered by filtering the resulting slurry at 135° C. The separated 2,6-naphthalene dicarboxylic acid was dried for 16 hours at 100° C. and analyzed. The results of these analyses are present in Table 1.

EXAMPLE 4

100 grams of crude 2,6-naphthalene dicarboxylic acid prepared by the method of Example 2 were combined with 1000 grams of boiling acetic anhydride. The resulting solution was filtered at a temperature of 135° C. to remove any undissolved solids. The resulting filtrate was cooled to −15° C. in order to crystallize the reaction product of 2,6-naphthalene dicarboxylic acid and acetic anhydride. The resulting slurry was filtered at −15° C. to recover this solid reaction product. The solid was then washed with acetic anhydride at 20° C. The washed solid was then hydrolyzed to form 2,6-naphthalene dicarboxylic acid, by admixture with 3 parts by weight of water per part of solid at 100° C. for 30 minutes. The solid was separated from the resulting slurry by filtration at 95° C., and then was dried in a vacuum oven maintained at 100° C. for 16 hours. The results of analyses of the resulting purified 2,6-naphthalene dicarboxylic acid are presented in Table 2.

EXAMPLE 5

100 grams of crude 2,6-naphthalene dicarboxylic acid prepared by the method of Example 2 were combined with 1000 grams of boiling acetic anhydride. The resulting solution was distilled at about 139° C. to boil off substantially all of the acetic acid that was formed as a by-product, and sufficient additional acetic anhydride was added to the solution to compensate for the volume of acetic acid that was removed by distillation. The resulting solution was filtered at a temperature of 135° C. to remove any undissolved solids. The temperature of the resulting filtrate was initially raised to its boiling point and then lowered with stirring to −15° C. in an isopropanol dry ice bath, to crystallize the reaction product of 2,6-naphthalene dicarboxylic acid and acetic anhydride. The resulting slurry was then filtered at −15° C. to recover this solid reaction product. The solid was then washed by slurrying 3 parts by weight of acetic anhydride per part of the solid with stirring for 30 minutes, and the wash solution was filtered at 20° C. from the slurry. The washed solid was then hydrolyzed to form 2,6-naphthalene dicarboxylic acid by admixture with 3 parts of water per part of solid at 100° C. for 30 minutes. The solid acid was then separated from the resulting slurry by filtration at 95° C., and then was dried in a vacuum oven maintained at 100° C. for 16 hours. The results of analyses of the resulting purified 2,6-naphthalene dicarboxylic acid are present in Table 2.

EXAMPLE 6

100 grams of crude 2,6-naphthalene dicarboxylic acid prepared by the method of Example 1 were combined with 1000 grams of boiling acetic anhydride. The resulting solution was filtered at a temperature of 135° C. to remove any undissolved solids.

624 grams of the filtrate and 4 grams of 0.5 weight percent of palladium deposited on activated carbon catalyst were charged to a stirred autoclave and maintained therein at 130° C. and 50 pounds per square inch for 60 minutes. Then 612.7 grams of the hydrogenation solution and catalyst were contacted with 5.6 grams of activated carbon chips at 139° C. for 60 minutes. The resulting slurry was then filtered at 135° C. to remove the hydrogenation catalyst and activated carbon. The temperature of the resulting filtrate was initially raised to its boiling point and then lowered with stirring to −15° C. in an isopropanol dry ice bath, to crystallize the reaction product of 2,6-naphthalene dicarboxylic acid and acetic anhydride. The resulting slurry was then filtered at −15° C. to recover this solid reaction product. The solid was then washed by slurrying 3 parts by weight of acetic anhydride per part of the solid with stirring for 30 minutes, and the wash solution was filtered at 20° C. from the slurry. The washed solid was then hydrolyzed to form 2,6-naphthalene dicarboxylic acid by admixture with 3 parts of water per part of solid at 100° C. for 30 minutes. The solid acid was then separated from the resulting slurry by filtration at 20° C. and then was dried in a vacuum oven maintained at 100° C. for 16 hours. The results of analyses of the resulting purified 2,6-naphthalene dicarboxylic acid are presented in Table 1.

EXAMPLE 7

Example 7 was performed using the procedure of Example 6, except that instead of hydrolyzing the washed reaction product, the washed reaction product was washed again by slurrying with fresh acetic anhydride and recovered by filtration. 65.2 grams of the recovered solids were then dissolved in 198.6 grams of boiling acetic anhydride. Then 200 grams of glacial acetic acid at its boiling point were added to the resulting solution over a 30 minute period, whereupon 2,6-naphthalene dicarboxylic acid was formed and crystallized. The resulting slurry was filtered at 135° C., and the separated solid acid was washed by slurrying with boiling water. The washed acid was recovered by filtration and was dried in a vacuum maintained at 100° C. for 16 hours. The results of the analyses of the resulting purified 2,6-naphthalene dicarboxylic acid are presented in Table 1.

In Tables 1 and 2, the concentration of each of the impurities in the feed composition is reported as weight percent, based on the total weight of feed. The composition of each of the impurities in the purified product is reported as weight percent, based on the total weight of purified product. In each case, the unreported remainder of the composition of each of the feed and the purified product is 2,6-naphthalene dicarboxylic acid. In addition, the following abbreviations are used for the indicated compounds: Naphth-Methyl-monoacid—6-methyl-2-naphthalene monocarboxylic acid; TMLA—trimellitic acid; TCB—tetracarboxybenzene; Br-2,6-NDA—(probably 7-) bromo-2,6-naphthalene dicarboxylic acid; Naphth-Triacid #1 and #2—first and second naphthalene tricarboxylic acids; FNA—6-formyl-2-naphthoic acid; 2-NA—2-naphthalene monocarboxylic acid; and Unknowns A and B—unidentified relatively lower and relatively higher molecular weight impurities. S.F. means the separation factor which is the ratio of the weight percent of a particular impurity in the unpurified 2,6-naphthalene dicarboxylic acid-to-the weight percent of the same impurity in the resulting purified 2,6-naphthalene dicarboxylic acid.

TABLE 1

| | | Purified Product | | | | | |
|---|---|---|---|---|---|---|---|
| | | Example 3 | | Example 6 | | Example 7 | |
| Component | Feed Composition | Comp. | S.F. | Comp. | S.F. | Comp. | S.F. |
| Unknown A | 0.062 | <0.01 | >6 | <0.01 | >6 | <0.01 | >6 |
| Naphth-Methyl-monoacid | 0.010 | <0.01 | >1 | <0.01 | >1 | <0.01 | >1 |
| TMLA | 2.42 | 0.089 | 27 | 0.051 | 47 | 0.011 | 220 |
| Unknown B | 0.036 | <0.01 | >4 | <0.01 | >4 | <0.01 | >4 |
| 1,2,3,4-TCB | 0.018 | <0.01 | >2 | <0.01 | >2 | <0.01 | >2 |
| 1,2,4,5-TCB | 0.021 | <0.01 | >2 | <0.01 | >2 | <0.01 | >2 |
| 1,2,3,5-TCB | <0.01 | <0.01 | >1 | <0.01 | >1 | <0.01 | >1 |
| Br-2,6-NDA | 0.62 | 0.43 | 1.5 | 0.019 | 33 | 0.019 | 33 |
| Naphth-Triacid #1 | 0.15 | 0.083 | 2 | 0.013 | 12 | 0.011 | 14 |

TABLE 1-continued

| Component | Feed Composition | Purified Product | | | | | |
|---|---|---|---|---|---|---|---|
| | | Example 3 | | Example 6 | | Example 7 | |
| | | Comp. | S.F. | Comp. | S.F. | Comp. | S.F. |
| Pentacarboxy benzene | <0.01 | <0.01 | >1 | <0.01 | >1 | <0.01 | >1 |
| Naphth-Triacid #2 | 0.032 | 0.014 | 2 | <0.01 | >3 | <0.01 | >3 |
| Other Unknowns | 0.14 | 0.034 | 4 | 0.075 | 2 | 0.024 | 2 |
| FNA | 0.17 | 0.04 | 4 | 0.013 | 13 | 0.0061 | 28 |
| 2-NA | <0.01 | | | | | | |

TABLE 2

| Component | Feed Composition | Purified Product | | | |
|---|---|---|---|---|---|
| | | Example 4 | | Example 5 | |
| | | Comp. | S.F. | Comp. | S.F. |
| Unknown A | 0.943 | <0.01 | >4 | <0.01 | >4 |
| Naphth-Methyl-monoacid | 0.020 | <0.01 | >2 | <0.01 | >2 |
| TMLA | 0.89 | <0.01 | >90 | 0.019 | 47 |
| Unknown B | 0.024 | <0.01 | >2 | <0.01 | >2 |
| 1,2,3,4-TCB | <0.01 | <0.01 | >1 | <0.01 | >1 |
| 1,2,4,5-TCB | <0.01 | <0.01 | >1 | <0.01 | >1 |
| 1,2,3,5-TCB | <0.01 | <0.01 | >1 | <0.01 | >1 |
| Br-2,6-NDA | 0.10 | 0.031 | 3 | 0.034 | 4 |
| Naphth-Triacid #1 | 0.12 | <0.01 | >12 | <0.01 | >12 |
| Pentacarboxy-benzene | <0.01 | <0.01 | >1 | <0.01 | >1 |
| Naphth-Triacid #2 | 0.037 | <0.01 | >4 | <0.01 | >4 |
| Other Unknowns | 0.086 | <0.01 | >9 | <0.01 | >9 |
| FNA | 0.34 | 0.037 | 9 | 0.060 | 6 |

From the above description, it is apparent that the objects of the present invention have been achieved. While only certain embodiments have been set forth, alternative embodiments and various modifications will be apparent from the above description to those skilled in the art and are considered equivalent and within the spirit and scope of the present invention.

Having described the invention, what is claimed is:

1. In a method for producing a naphthalene dicarboxylic acid comprising oxidizing a dialkylnaphthalene wherein each alkyl group may be the same or different and is methyl, ethyl or propyl, or a partially oxidized derivative thereof, with an oxygen-containing gas in a solvent in the liquid phase at an elevated temperature and pressure and in the presence of an oxidation catalyst comprising a bromine component and at least one of a cobalt- or manganese-containing component to form a crude naphthalene dicarboxylic acid: the improvement comprising purifying the resulting solid crude naphthalene dicarboxylic by:

(a) reacting the crude naphthalene dicarboxylic acid with a first lower alkanoic anhydride of an alkanoic acid containing from 2 to 5 carbon atoms, at a mole ratio in the range of from about 1 to about 2 moles of the first lower alkanoic anhydride per mole of crude naphthalene dicarboxylic acid, and at a temperature in the range of from 100° C. to about 200° C., to thereby form (1) a reaction product of the crude naphthalene dicarboxylic acid and first lower alkanoic anhydride which is soluble in the excess unreacted first lower alkanoic anhydride, and (2) an alkanoic acid formed from the first lower alkanoic anhydride;

(b) reacting the aforesaid dissolved reaction product with from about 1 to about 2 moles of water or of an alkanoic acid containing from 2 to 5 carbon atoms per mole of crude naphthalene dicarboxylic acid employed in step (a), and at a temperature in the range of from about 100° C. to about 200° C., to thereby form the purified form of the crude naphthalene dicarboxylic acid employed in step (a), which crystallizes to produce a solid-liquid mixture;

(c) removing solid purified naphthalene dicarboxylic acid from the resulting solid-liquid mixture at a temperature in the range of from about 20° C. to about 200° C.

2. The method of claim 1 wherein, (d) after step (a) and before step (b), the reaction product of crude naphthalene dicarboxylic acid that was formed in step (a) is crystallized by cooling the resulting solution to a temperature in the range of from about 60° C. to about −30° C., with agitation, to form a solid-liquid mixture;

(e) the resulting solid reaction product is separated from the resulting solid-liquid mixture at a temperature in the range of from about 60° C. to about −30° C.; and (f) the separated solid reaction product is combined with from about 5 to about 50 moles of a second lower alkanoic anhydride containing from 2 to 5 carbon atoms per mole of crude naphthalene dicarboxylic acid employed in step (a), and at a temperature in the range of from about 20° C. to about 200° C., to thereby dissolve the aforesaid purified reaction product; such that the sequence of steps is (a), (d), (e), (f), (b) and (c).

3. The method of claim 1 wherein, after step (a) and before step (b), any undissolved solids are removed from the solution formed in step (a) at a temperature in the range of from about 80° C. to about 200° C.

4. The method of claim 2 wherein, after step (a) and before step (d), any undissolved solids are removed from the solution formed in step (a) at a temperature in the range of from about 80° C. to about 200° C.

5. The method of claim 1 wherein, after step (a) and prior to step (b), the dissolved reaction product of crude naphthalene dicarboxylic acid is hydrogenated in the presence of hydrogen and a hydrogenation catalyst and at a temperature in the range of from about 80° C. to about 200° C.

6. The method of claim 5 wherein the hydrogenation catalyst comprises Group VIII noble metal on a solid support.

7. The method of claim 6 wherein the hydrogenation catalyst comprises palladium on carbon.

8. The method of claim 5 wherein the hydrogenation is performed at a temperature in the range of from about 80° C. to about 200° C.

9. The method of claim 2 wherein, after step (a) and before step (d), the dissolved reaction product of crude naphthalene dicarboxylic acid is hydrogenated in the presence of hydrogen and a hydrogenation catalyst and at a temperature in the range of from about 80° C. to about 200° C.

10. The method of claim 1 wherein, after step (a) prior to step (b), activated carbon is contacted with the solution of the reaction product of crude naphthalene dicarboxylic acid at a temperature in the range of from about 80° C. to about 200° C., and then the aforesaid solution is separated from the activated carbon.

11. The method of claim 10 wherein the activated carbon is contacted at a temperature in the range of from about 90° C. to about 180° C.

12. The method of claim 2 wherein, after step (a) and before step (d), activated carbon is contacted with the solution of the reaction product of crude naphthalene dicarboxylic acid at a temperature in the range of from about 80° C. to about 200° C., and then the aforesaid solution is separated from the activated carbon.

13. The method of claim 2 wherein after step (e) and prior to step (f), the separated solid reaction product is washed with a third lower alkanoic anhydride of an alkanoic acid containing from 2 to 5 carbon atoms, at a temperature in the range of from about 60° C. to about −30° C.

14. The method of claim 13 wherein washing is performed at a temperature in the range of from about 60° C. to about −15° C.

15. The method of claim 13 wherein the third lower alkanoic anhydride employed is the same as the second lower alkanoic anhydride employed in step (e).

16. The method of claim 1 wherein the crude naphthalene dicarboxylic acid and first lower alkanoic anhydride are reacted in step (a) at a more ratio in the range of from about 0.02:1 to about 0.2:1.

17. The method of claim 1 wherein the crude naphthalene dicarboxylic acid and first lower alkanoic anhydride are reacted in step (a) at a temperature in the range of from about 80° C. to about 200° C.

18. The method of claim 1 wherein the crude naphthalene dicarboxylic acid is 2,6-naphthalene dicarboxylic acid.

19. The method of claim 18 wherein the first lower alkanoic anhydride is acetic anhydride.

20. The method of claim 1 wherein step (b) is performed at a temperature in the range of from about 80° C. to about 200° C.

21. The method of claim 3 wherein the solids are removed by filtration.

22. The method of claim 2 wherein the solution is cooled in step (d) to a temperature in the range of from about 60° C. to about −15° C.

23. The method of claim 2 wherein step (e) is performed at a temperature in the range of from about 60° C. to about −15° C.

24. The method of claim 2 wherein the solid reaction product is removed in step (e) by filtration.

25. The method of claim 2 wherein the second lower alkanoic anhydride employed in step (f) is the same as the first lower alkanoic anhydride employed in step (a).

26. The method of claim 2 wherein step (f) is performed at a temperature in the range of from about 80° C. to about 200° C.

27. The method of claim 2 wherein in step (f), the separated solid reaction product is combined with from about 5 to about 50 moles of the second lower alkanoic anhydride per mole of crude naphthalene dicarboxylic acid employed in step (a).

28. The method of claim 1 wherein step (b) is performed at a temperature in the range of from about 80° C. to about 200° C.

29. The method of claim 1 wherein step (b), the dissolved reaction product is reacted with from about 1 to about 2 moles of water or of the aforesaid alkanoic acid.

30. The method of claim 1 wherein in step (b), the dissolved reaction product is reacted with the aforesaid alkanoic acid in its glacial form.

31. The method of claim 1 wherein the second lower alkanoic anhydride employed in step (f) is the anhydride of the alkanoic acid employed in step (b).

32. The method of claim 1 wherein the alkanoic acid formed in step (a) is removed as it is being formed.

* * * * *